United States Patent
Pang et al.

(10) Patent No.: US 10,264,976 B2
(45) Date of Patent: Apr. 23, 2019

(54) BIOCOMPATIBLE FLAVONOID COMPOUNDS FOR ORGANELLE AND CELL IMAGING

(71) Applicants: Yi Pang, Copley, OH (US); Bin Liu, Akron, OH (US)

(72) Inventors: Yi Pang, Copley, OH (US); Bin Liu, Akron, OH (US)

(73) Assignee: The University of Akron, Akron ( * ) Notice: Subject to any disclaimer, the term of this patent is extended or adjusted under 35 U.S.C. 154(b) by 593 days.

(21) Appl. No.: 14/934,665

(22) Filed: Nov. 6, 2015

(65) Prior Publication Data
US 2016/0376296 A1    Dec. 29, 2016

Related U.S. Application Data

(60) Provisional application No. 62/184,290, filed on Jun. 25, 2015.

(51) Int. Cl.
| | | |
|---|---|---|
| *A61B 5/00* | (2006.01) | |
| *A61K 49/00* | (2006.01) | |
| *C07D 311/30* | (2006.01) | |
| *C12N 15/113* | (2010.01) | |
| *C07F 9/6533* | (2006.01) | |
| *C12Q 1/02* | (2006.01) | |
| *G01N 33/58* | (2006.01) | |
| *A61K 31/713* | (2006.01) | |

(52) U.S. Cl.
CPC ........ *A61B 5/0071* (2013.01); *A61K 49/0021* (2013.01); *C07D 311/30* (2013.01); *C07F 9/6533* (2013.01); *C12N 15/113* (2013.01); *C12N 15/1135* (2013.01); *C12N 15/1137* (2013.01); *C12Q 1/02* (2013.01); *G01N 33/582* (2013.01); *H05K 999/99* (2013.01); *A61K 31/713* (2013.01); *C12N 2310/14* (2013.01); *C12N 2310/322* (2013.01); *C12N 2310/344* (2013.01); *C12N 2310/3515* (2013.01); *C12N 2310/531* (2013.01); *C12N 2320/30* (2013.01); *C12N 2320/32* (2013.01); *C12N 2320/35* (2013.01); *C12N 2320/53* (2013.01)

(58) Field of Classification Search
None
See application file for complete search history.

(56) References Cited

U.S. PATENT DOCUMENTS

2011/0003861 A1* 1/2011 Giordani .............. C07D 405/10
514/337

OTHER PUBLICATIONS

Liu et al. Biocompatible flavone-based fluorogenic probes for quick wash-free mitochondrial imaging in living cells. 2014 ACS Appl. Mater. Interfaces. 6: 21638-21644. Epub Nov. 19, 2014. (Year: 2014).*

* cited by examiner

*Primary Examiner* — Michael G. Hartley
*Assistant Examiner* — Jennifer Lamberski
(74) *Attorney, Agent, or Firm* — Renner, Kenner, Greive, Bobak, Taylor & Weber Co. LPA

(57) ABSTRACT

Flavonoid compounds may be prepared that are selective for certain cell organelles, and may be used as biological imaging agents. Organelles that may be imaged with flavonoid compounds include mitochondria and lysosomes. Advantageously, the flavonoids show specificity to certain organelles and may exhibit a florescence "turn-on" mechanism, where the flavonoids that have target an organelle exhibit a florescence response when excited.

15 Claims, 12 Drawing Sheets
(12 of 12 Drawing Sheet(s) Filed in Color)

(a)

(b)

a: R=Methyl (DMAF); b: R= Et (DEAF); c: R=Ph (DPAF)

BIOCOMPATIBLE FLAVONOID COMPOUNDS FOR ORGANELLE AND CELL IMAGING

CROSS-REFERENCE TO RELATED APPLICATIONS

The present application claims priority to U.S. Provisional Patent Application No. 62/184,209, filed Jun. 25, 2015, incorporated herein by reference.

STATEMENT REGARDING FEDERALLY SPONSORED RESEARCH OR DEVELOPMENT

This invention was made with government support under 1R15EB014546-01A1 awarded by National Institutes of Health. The government has certain rights in the invention.

FIELD OF THE INVENTION

Embodiments relate to flavonoid compounds and methods for organelle imagining using flavonoid compounds. Organelles that may be imaged include mitochondria and lysosomes.

BACKGROUND OF THE INVENTION

Monitoring biomolecular and biochemistry process in organisms is a fundamental issue in biosensing, which has applications from fundamental biological research to clinical diagnostics. Mitochondria, a membrane-bound organelle found in most eukaryotic cells, play important roles in numerous vital cellular processes, such as energy supplying, reactive oxygen species generation, signaling, cellular differentiation and cell death. The mitochondrial network displays remarkable plasticity during development of certain tissues. The morphology of mitochondria is affected by cell type, cell-cycle stage, and intracellular metabolic state, which in turn contributes to cell functioning. Recent reports show that the mitochondria are also crucially involving in various pathologies, from Alzheimer's disease to cancer. Thus, development of a convenient and efficient mitochondrial imaging method is of great fundamental importance for understanding cell biochemistry process and early diagnosing disease.

Fluorescence techniques are particularly well suited for biological application, due to their non-invasive feature and high sensitivity. So far, a few fluorescent dyes have been developed for mitochondrial imaging, such as rhodamines, rosamines, carbocyanines, and BODIPY dyes, with some showing two-photon emission (TPE) properties. However, most mitochondrial probes, such as BODIPY dyes, give strong fluorescence signals in buffer solution. During the application, the unbound probes must be washed off to eliminate the strong residual signal from the free dyes to improve the signal-to-noise (S/N) ratio. The time-consuming washing process will inevitably delay the acquisition of microscopic data. In addition, the required post-application washing procedure could alter the cell environment and hamper the probe's ability to monitor mitochondrial changes in real-time. This is because the number and subcellular locations of mitochondria will dramatically change with the cell metabolic demands. Moreover, since mitochondria are directly associated with cytoactivity, the dying cells could be removed during the washing process, adversely affecting the monitor of whole cell apoptosis cycle. In order to overcome the deficiency, aggregation-induced emission (AIE) dyes have been used to minimize the fluorescence signals of free dyes. The operation of AIE dyes, however, requires the significant accumulation of dye molecules on the cells to form aggregation. It remains a challenge to develop a novel strategy that permits the specific mitochondria labeling without the post application washing, thereby enabling continuous observation of the entire biochemistry process without interruption. Although an AIE dye has been used to track the mitochondria without washing process, it is desirable to identify a new mechanism that does not require the accumulation of dye molecules on the cells, which usually takes a longer time (e.g. 20 min) and high concentration to stain a target.

Lysosomes, another component in eukaryotic cells, are important part of the endocytic system of the cell and serve a degradative function. Lysosomes are membrane-bound organelles with an acidic interior (pH of about 4.5), and contain approximately 50 different degradative enzymes that degrade the material that is brought into the cell. The degradation process is not random and in a number of instances is targeted. Deficiency in a single lysosomal enzyme could prevent breakdown of target molecules, which consequently accumulate within the lysosomes and often give rise to clinical symptoms. Deficiencies in lysosomal enzymes cause abnormal storage of macromolecular substrates, which are known as lysosomal storage diseases.

Most lysosomal sensors are weak bases (by including an amino group) that can be used to accumulate dyes in acidic organelles. Upon entering the acidic organelles, the protonation also reduces (or removes) the photoinduced electron transfer (PET) from the attached amino groups, thereby increasing the fluorescence intensity of the fluorescent dyes. For example, the commercial LysoTracker®, such as Red DND-99, has an amino group to concentrate the sensor to lysosome organelles. Unfortunately, the existing lysosomal probes often exhibit high background fluorescence signals, due to incomplete fluorescence quenching. The conditions that require the PET to switch off completely at the narrow pH (about 4.5) also raise a challenge.

Thus, a need remains in the art for improved biological imaging agents for the imaging organelles that do not suffer from one or more of the above mentioned deficiencies.

SUMMARY OF THE INVENTION

In a first embodiment, a flavonoid compound is provided by the formula

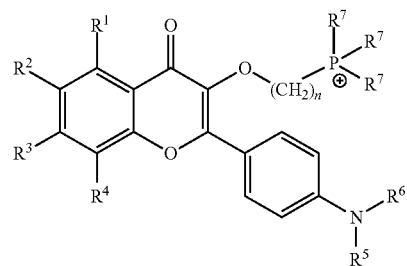

where each $R^1$-$R^4$ is individually an organic group or an hydrogen atom, $R^5$ and $R^6$ are each individually an organic group or an hydrogen atom or where $R^5$ and $R^6$ combine to form a single organic group, each $R^7$ is individually an organic group, and n is about 3 to 10 units.

In a second embodiment, a flavonoid compound is provided as in the first embodiment, where the flavonoid compound is defined by the formula

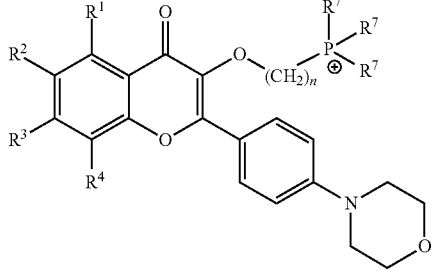

where each $R^1$-$R^4$ is individually an organic group or an hydrogen atom, each $R^7$ is individually an organic group, and n is about 3 to 10 units.

In a third embodiment, a flavonoid compound is provided as in either the first or second embodiment, where the flavonoid compound is defined by the formula

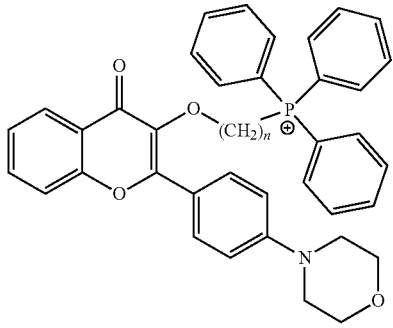

where n is about 3 to 10 units.

In a fourth embodiment, a flavonoid compound is provided as in any of the first through third embodiments, where the flavonoid compound is defined by the formula

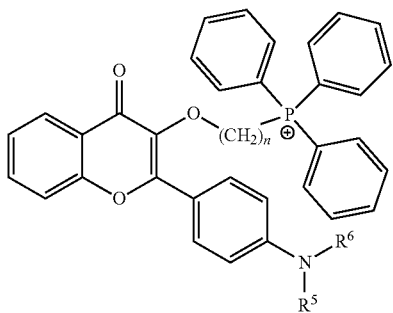

where $R^5$ and $R^6$ are each individually an organic group or an hydrogen atom or where $R^5$ and $R^6$ combine to form a single organic group and n is about 3 to 10 units.

In a fifth embodiment, a flavonoid compound is provided by the formula

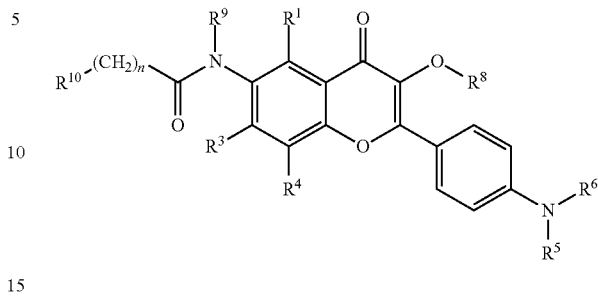

where each $R^1$, $R^3$, and $R^4$ is individually an organic group or an hydrogen atom, $R^5$ and $R^6$ are each individually an organic group or an hydrogen atom or where $R^5$ and $R^6$ combine to form a single organic group, $R^8$ is an organic group or a hydrogen atom, $R^9$ is an organic group or a hydrogen atom, $R^{10}$ is an organic group or a hydrogen atom, and n is about 1 to 10 units.

In a sixth embodiment, a flavonoid compound is provided as in the fifth embodiment, where the flavonoid compound is defined by the formula

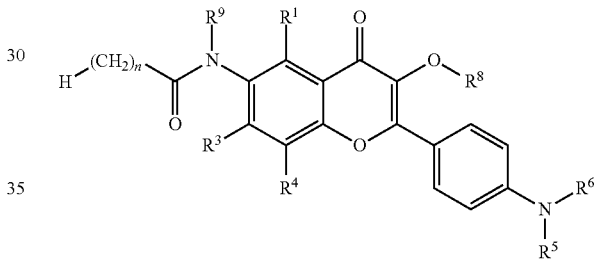

where each $R^1$, $R^3$, and $R^4$ is individually an organic group or an hydrogen atom, $R^5$ and $R^6$ are each individually an organic group or an hydrogen atom or where $R^5$ and $R^6$ combine to form a single organic group, $R^8$ is an organic group or a hydrogen atom, $R^9$ is an organic group or a hydrogen atom, and n is about 1 to 10 units.

In a seventh embodiment, a flavonoid compound as in either of the fifth or sixth embodiments is provided, where the flavonoid compound is defined by the formula

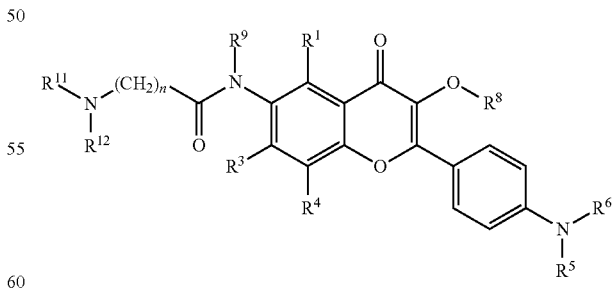

where each $R^1$, $R^3$, and $R^4$ is individually an organic group or an hydrogen atom, $R^5$ and $R^6$ are each individually an organic group or an hydrogen atom or where $R^5$ and $R^6$ combine to form a single organic group, $R^8$ is an organic group or a hydrogen atom, $R^9$ is an organic group or a hydrogen atom, $R^{11}$ and $R^{12}$ are each individually an organic group or an hydrogen atom or where $R^{11}$ and $R^{12}$ combine to form a single organic group, and n is about 1 to 6 units.

In an eighth embodiment, a flavonoid compound as in any of the fifth through seventh embodiments is provided, where the flavonoid compound is defined by the formula

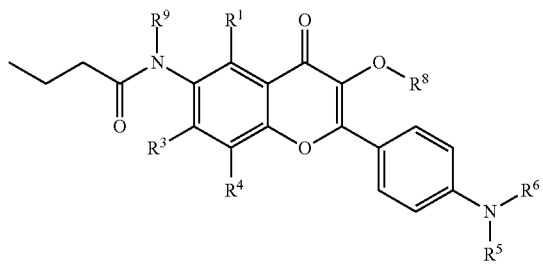

where each $R^1$, $R^3$, and $R^4$ is individually an organic group or an hydrogen atom, $R^5$ and $R^6$ are each individually an organic group or an hydrogen atom or where $R^5$ and $R^6$ combine to form a single organic group, $R^8$ is an organic group or a hydrogen atom, and $R^9$ is an organic group or a hydrogen atom.

In a ninth embodiment, a method of imaging an organelle is provided comprising: combining a mitochondrion and a flavonoid compound and allowing the flavonoid compound to stain the mitochondrion, where the flavonoid compound is defined by the formula

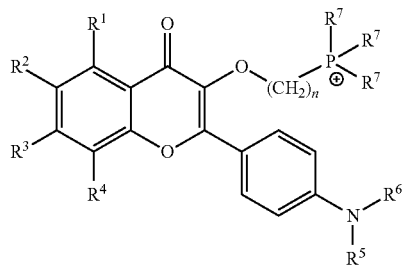

where each $R^1$-$R^4$ is individually an organic group or an hydrogen atom, $R^5$ and $R^6$ are each individually an organic group or an hydrogen atom or where $R^5$ and $R^6$ combine to form a single organic group, each $R^7$ is individually an organic group, and n is about 3 to 10 units; irradiating the stained mitochondrion with an excitation wavelength that excites the flavonoid and induces a fluorescence response; and capturing an image of the fluorescence response.

In a tenth embodiment, a method as in the ninth embodiment is provided, where the mitochondrion is an isolated cell-free mitochondrion.

In an eleventh embodiment, a method as in either the ninth or tenth embodiments is provided, where the mitochondrion is present in a eukaryotic cell.

In a twelfth embodiment, a method as in any of the ninth through eleventh embodiments is provided, where the eukaryotic cell is a stem cell.

In a thirteenth embodiment, a method as in any of the ninth through twelfth embodiments is provided, where the step of allowing the flavonoid compound to stain the mitochondrion is performed by incubating a mitochondrion with about 0.02 µM to about 10 µM of the flavonoid at about 37° C. for about 25 min in a growth medium.

In a fourteenth embodiment, a method of imaging an organelle is provided comprising: combining a eukaryotic cell containing lysosome and a flavonoid compound and allowing the flavonoid compound to stain the lysosome, where the flavonoid compound is defined by the formula

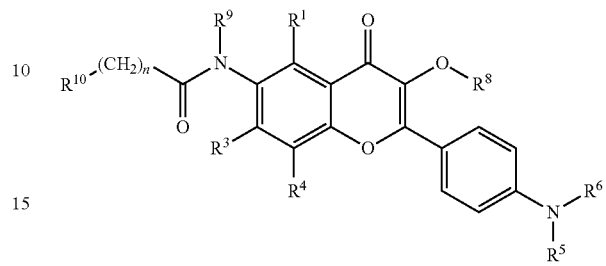

where each $R^1$, $R^3$, and $R^4$ is individually an organic group or an hydrogen atom, $R^5$ and $R^6$ are each individually an organic group or an hydrogen atom or where $R^5$ and $R^6$ combine to form a single organic group, $R^8$ is an organic group or a hydrogen atom, $R^9$ is an organic group or a hydrogen atom, $R^{10}$ is an organic group or a hydrogen atom, and n is about 1 to 10 units; irradiating the stained lysosome with an excitation wavelength that excites the flavonoid and induces a fluorescence response; and capturing an image of the fluorescence response.

In a fifteenth embodiment, a method as in the fourteenth embodiment is provided, where the lysosome is an isolated cell-free lysosome.

In a sixteenth embodiment, a method as in either the fourteenth or fifteenth embodiments is provided, where the lysosome is in a eukaryotic cell.

In a seventeenth embodiment, a method as in any of the fourteenth through sixteenth embodiments is provided, where the eukaryotic cell is a stem cell.

In an eighteenth embodiment, a method as in any of the fourteenth through seventeenth embodiments is provided, where the step of allowing the flavonoid compound to stain the lysosome is performed by incubating a lysosome with about 0.02 µM to about 10 µM of the flavonoid at about 37° C. for about 25 min in a growth medium.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF ILLUSTRATIVE EMBODIMENTS

Embodiments are based, at least in part, on the discovery that flavonoid compounds may be used as detection and imagining compounds. Because flavonoids are environmentally sensitive fluorophores, they will only provide a florescent response under certain conditions. It has been found that, flavonoids compound may be used to selectively stain organelles of eukaryotic cells such as mitochondria and lysosomes. Advantageously, the flavonoids that do not selectively stain an organelle have no fluorescence response or no significant fluorescence response when the flavonoid is irradiated. No significant fluorescence response refers to a fluorescence response that is not significantly higher than the background or a response that does not impede detection of an organelle. Flavonoid compounds are particularly advantageous because they are biocompatible, as a result eukaryotic cells stained with flavonoid compounds have low instances of cells death.

As an important natural pigment, flavonoids constitute a major portion of natural products present in fruits and vegetables, and are responsible for the colors (e.g. red and orange) in fruits and vegetables. A flavonoid-rich diet may provide protection against cardiovascular diseases and some forms of cancer. Flavonoid base compounds may provide molecular imaging reagents of low toxicity, which is desirable for imaging in living organisms.

Those skilled in the art will recognize that a base flavone compound may be defined by the formula:

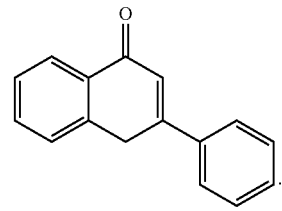 [SMILES: O=C1C=C(c2ccccc2)Cc2ccccc21]

In one or more embodiments, flavonoids include those compounds where one or more of the hydrogen atoms of the base flavone compound are substituted or replaced with an organic groups. In one or more embodiments, the flavonoid compound may include an organic group capable of targeting an organelle of a eukaryotic cell.

Suitable organic groups for use in flavonoid compounds include amines and hydrocarbon groups. Exemplary hydrocarbon groups include aliphatic hydrocarbon groups, cyclic hydrocarbon groups, aromatic hydrocarbon groups, and groups comprising combinations thereof. The organic groups may also include a heteroatom replacing a carbon in a hydrocarbon structure. Specific heteroatoms include oxygen, sulfur, and nitrogen. The organic group may also include halogen atoms. Specific examples of halogen atoms include fluorine, chlorine, bromine, and iodine. In these or other embodiments, the organic group may be an alkyl group. Suitable alkyl groups include linear branched or alkyls. Specific examples of alkyl groups include methyl, ethyl, propyl, isopropyl, isobutyl, tert-butyl, n-butyl, sec-butyl, isopentyl, tertpentyl, n-pentyl, sec-pentyl, terthexyl, n-hexyl, isohexyl, and sec-hexyl. In these or other embodiments, the organic group may include a cycloalkyl or an aromatic group.

Figure 1:
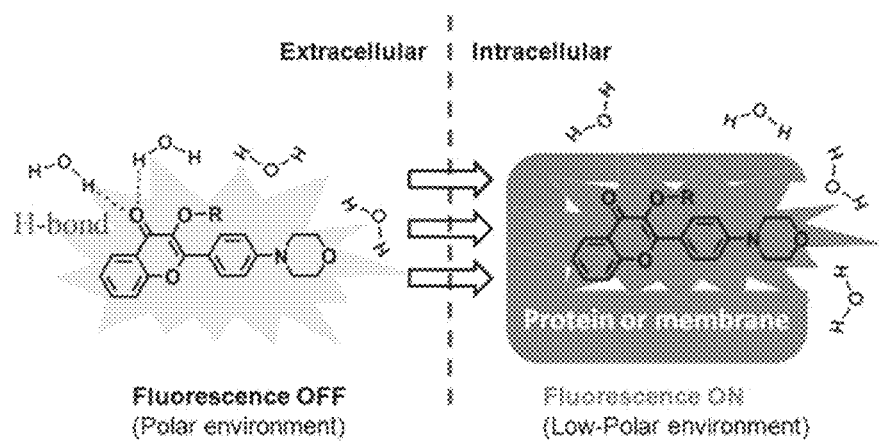
FIG. 1 provides a scheme describing the principle behind the wash-free fluorescence imaging method based on flavone dyes.

As noted above, flavonoids are environmentally-sensitive fluorophores. Flavonoids exhibit little to no fluorescence in polar solvents. However, flavonoids become highly fluorescent in a low-polar solvent. Since highly polar water molecules are strong H-bond donors, the fluorescence of flavonoids can be severely quenched by the intermolecular electron or proton transfer between dyes and water (FIG. 1). The fluorescence of flavonoids may be efficiently switchedon when they are incorporadeded by proteins or lipid membranes in the non-polar microenvironment in cells.

A flavanoid may stain an organelle when the flavanoid is incorporated into the an organelle to a sufficient extent that the ability of the flavanoid to fluoresce is "switched on." In other words, an organelle has been stained by a flavanoid when it is incorporates into the organelle and fluorescence is not inhibited by a polar solvent. After an organelle has been stained it may be irradiated with an excitation wavelength that excites the flavonoid and induces a fluorescence response. The fluorescence response may be imaged by conventional methods capable of capturing the wavelength of the fluorescence response.

In one or more embodiments, the flavonoid has an excitation wavelength of about 400 nm to about 460, which results in a fluorescence emission of about 450 nm to about 625 nm. In these or other embodiments, the flavonoid has an excitation wavelength of about 400 nm to about 420, which results in a fluorescence emission of about 500 nm to about 600 nm.

Specific examples of organelles that may be stained include mitochondria and lysosomes. In one or more embodiments, the organelle that may be stained may be a cell-free (i.e. isolated) organelle. In one or more embodiments, the organelle that may be stained is in a eukaryotic cell. In these or other embodiments, the eukaryotic cells may be single cells or part of a tissue or multi-cell organism.

The ability to stain organelles with a flavonoid is not limited to any particular eukaryotic cell. Suitable eukaryotic cells include human cells and stem cells. Specific examples of eukaryotic cells include human cells such as mesenchymal stem cells (hMSCs), and oligodendrocytes cells. Specific examples of multicelled organisms include zebra fish.

In one or more embodiments, the organelle may be stained with a flavonoid by simply contacting the organelle with a flavonoid compound. While a washing step may be performed, due to the environmentally sensitive nature of flavonoid fluorescence, there is no need to wash away the excess flavonoid prior to imagining. In one or more embodiments, a free organelle or a eukaryotic cell may be incubated in a solution including a flavanoid compound. Because incubation parameters for eukaryotic cells (particularly those eukaryotic cell that are in multi-cell organisms) may vary based upon the particular needs of the cells. Generally, organelles of eukaryotic cell may be stained by incubating the cells in a growth medium that includes a flavonoid.

In one more embodiments, the incubation may be characterized by the amount of time the free organelle or a eukaryotic cell is incubated prior to imaging. In one or more embodiments, the free organelle or a eukaryotic cell may be incubated for less than 100 min, in other embodiments less than 50 min, and in other embodiments less than 30 min. In one or more embodiments, the free organelle or a eukaryotic cell may be incubated for greater than 10 min, in other embodiments greater than 20 min, and in other embodiments greater than 30 min. In one or more embodiments, the free organelle or a eukaryotic cell may be incubated for about 10 min to about 60 min, in other embodiments for about 20 min to about 50 min, and in other embodiments greater for about 30 min to about 40 min.

In one more embodiments, the incubation may be characterized by the temperature of which the free organelle or a eukaryotic cell is incubated. In one or more embodiments, the free organelle or a eukaryotic cell may be incubated at less than 60° C., in other embodiments less than 38° C., and in other embodiments less than 37° C. In one or more embodiments, the free organelle or a eukaryotic cell may be incubated for greater than 20° C., in other embodiments greater than 25° C., and in other embodiments greater than 30° C. In one or more embodiments, the free organelle or a eukaryotic cell may be incubated at about 25° C. to about 40° C., in other embodiments for about 27° C. to about 35° C., and in other embodiments greater for about 29° C. to about 30° C.

In one more embodiments, the incubation may be characterized by the concentration of the flavonoid used to incubate the organelle or a eukaryotic cell. In one or more embodiments, the free organelle or a eukaryotic cell may be incubated in less than 30 µM, in other embodiments less than 20 µM, and in other embodiments less than 10 µM. In one or more embodiments, the free organelle or a eukaryotic cell may be incubated in greater than 0.01 µM, in other embodiments greater than 0.05 µM, and in other embodiments greater than 1 µM. In one or more embodiments, the free organelle or a eukaryotic cell may be incubated in about 5 µM to about 30 µM, in other embodiments in about 7 µM to about 20 µM, and in other embodiments greater for about 9 µM to about 10 µM.

In an exemplary incubation, a eukaryotic cell may be incubated with 0.02-10 µM flavonoid compound at 37° C. for about 25 min in serum-containing stem cell growth medium such as mesenchymal stem cell growth medium.

As noted above, organelles that may be stained by flavonoids include mitochondria. In one or more embodiments, a flavonoids that may be used to stain a mitochondrium may be defined by formula I:

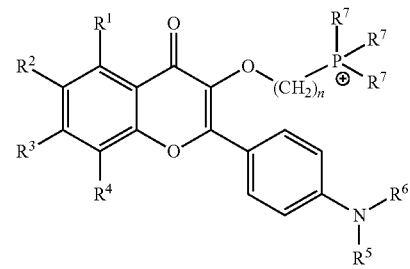

where each $R^1$-$R^4$ is individually an organic group or an hydrogen atom, $R^5$ and $R^6$ are each individually an organic group or an hydrogen atom or where $R^5$ and $R^6$ combine to form a single organic group, each $R^7$ is individually an organic group, and n is about 3 to 10 units.

In one or more embodiments, where the $R^5$ and $R^6$ groups of formula I combine to make a morpholine group, the flavonoid that may be used to stain a mitochondrium may be defined by formula II:

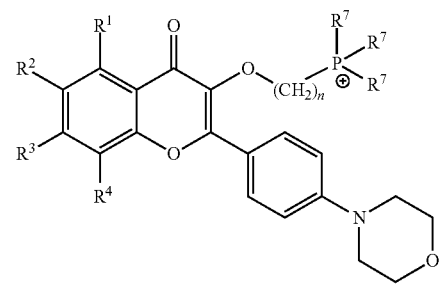

where each $R^1$-$R^4$ is individually an organic group or an hydrogen atom, each $R^7$ is individually an organic group, and n is about 3 to 10 units.

In one or more embodiments, where the $R^7$ groups of formula II are each phenyl groups, the flavonoids that may be used to stain a mitochondrium may be defined by formula III:

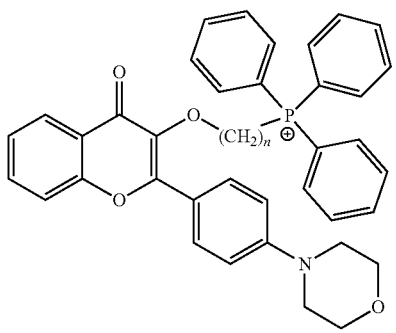

where n is about 3 to 10 units.

In one or more embodiments, where the $R^7$ groups of formula I are each phenyl groups, the flavonoid that may be used to stain a mitochondrium may be defined by formula IV:

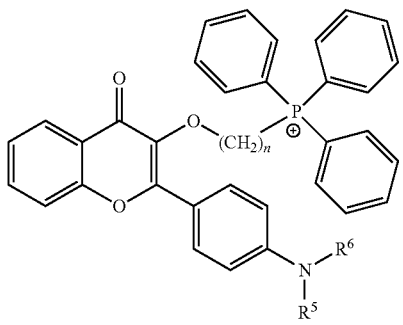

where $R^5$ and $R^6$ are each individually an organic group or an hydrogen atom or where $R^5$ and $R^6$ combine to form a single organic group and n is about 3 to 10 units.

As noted above, organelles that may be stained by flavonoids include lysosomes. In one or more embodiments, the flavonoid that may be used to stain a lysosome may be defined by formula V:

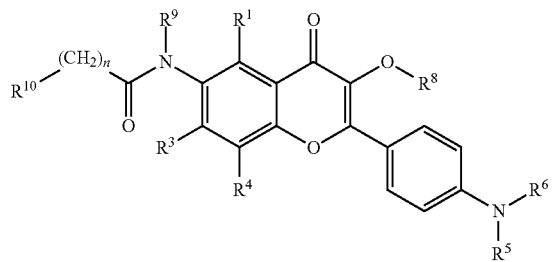

where each $R^1$, $R^3$, and $R^4$ is individually an organic group or an hydrogen atom, $R^5$ and $R^6$ are each individually an organic group or an hydrogen atom or where $R^5$ and $R^6$ combine to form a single organic group, $R^8$ is an organic group or a hydrogen atom, $R^9$ is an organic group or a hydrogen atom, $R^{10}$ is an organic group or a hydrogen atom, and n is about 1 to 10 units.

In one or more embodiments, where the $R^{10}$ group of formula V is a hydrogen atom, the flavonoid that may be used to stain a lysosome may be defined by formula VI:

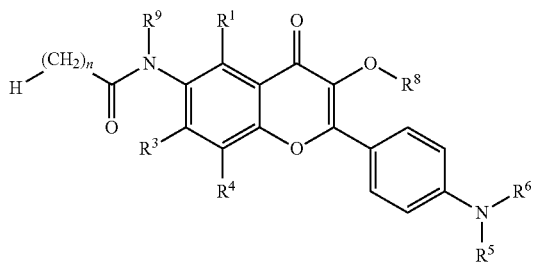

where each $R^1$, $R^3$, and $R^4$ is individually an organic group or an hydrogen atom, $R^5$ and $R^6$ are each individually an organic group or an hydrogen atom or where $R^5$ and $R^6$ combine to form a single organic group, $R^8$ is an organic group or a hydrogen atom, $R^9$ is an organic group or a hydrogen atom, and n is about 1 to 10 units.

In one or more embodiments, where the $R^{10}$ group of formula V is an amine group, the flavonoid that may be used to stain a lysosome may be defined by formula VII:

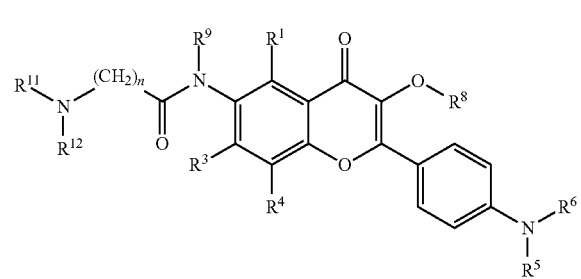

where each $R^1$, $R^3$, and $R^4$ is individually an organic group or an hydrogen atom, $R^5$ and $R^6$ are each individually an organic group or an hydrogen atom or where $R^5$ and $R^6$ combine to form a single organic group, $R^8$ is an organic group or a hydrogen atom, $R^9$ is an organic group or a hydrogen atom, $R^{11}$ and $R^{12}$ are each individually an organic group or an hydrogen atom or where $R^{11}$ and $R^{12}$ combine to form a single organic group, and n is about 1 to 6 units.

In one or more embodiments, where the n of formula VI is 3 units, the flavonoid that may be used to stain a lysosome may be defined by formula VIII:

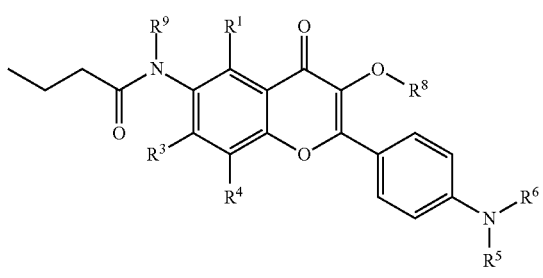

where each $R^1$, $R^3$, and $R^4$ is individually an organic group or an hydrogen atom, $R^5$ and $R^6$ are each individually an organic group or an hydrogen atom or where $R^5$ and $R^6$ combine to form a single organic group, $R^8$ is an organic group or a hydrogen atom, and $R^9$ is an organic group or a hydrogen atom.

While particular embodiments of the invention have been disclosed in detail herein, it should be appreciated that the invention is not limited thereto or thereby inasmuch as variations on the invention herein will be readily appreciated by those of ordinary skill in the art. The scope of the invention shall be appreciated from the claims that follow.

EXAMPLES

Mitochondria Imagining

Figure 2:
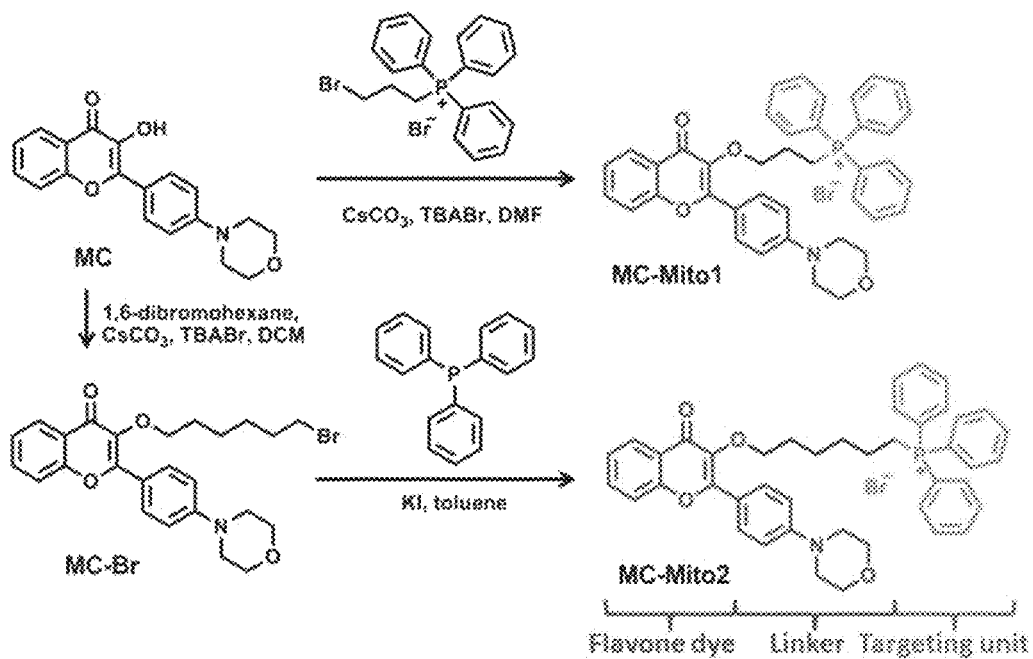
FIG. 2 provides a scheme describing the design and synthesis for MC-Mito1 and MC-Mito2.

MC-Mito1 was synthesized by reaction of (3-bromopropyl)triphenylphosphonium with 3-hydroxy-2-(4-morpholinophenyl)-4H-chromen-4-one (MC) (FIG. 2), which was obtained in two steps by a Claisen-Schmidt condensation and Algar-Flynn-Oyamada reaction. MC-Mito2 was prepared in two steps from MC by conjugation with a longer linker unit, followed by reaction with triphenylphosphine. Both MC-Mito1 and MC-Mito2 are consisting of the flavone fluorophore, alkyl linker, and triphenylphosphonium as mitochondria-targeting group. The length of the alkyl linker is known to be crucial for achieving a balanced labeling efficiency and target selectivity for bioimaging.

Figure 3:
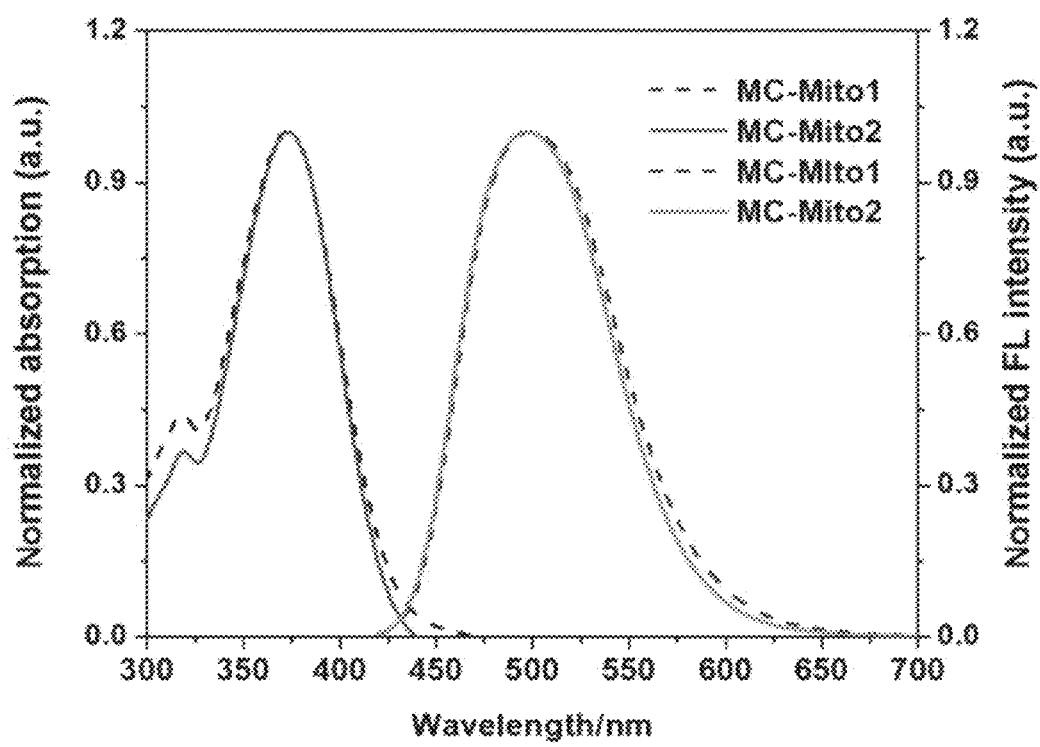
FIG. 3 provides a graph showing the normalized UV spectra and FL spectra of MC-Mito1 (dash line) and MC-Mito2 (solid line) in DMSO solution.
Figure 4A:
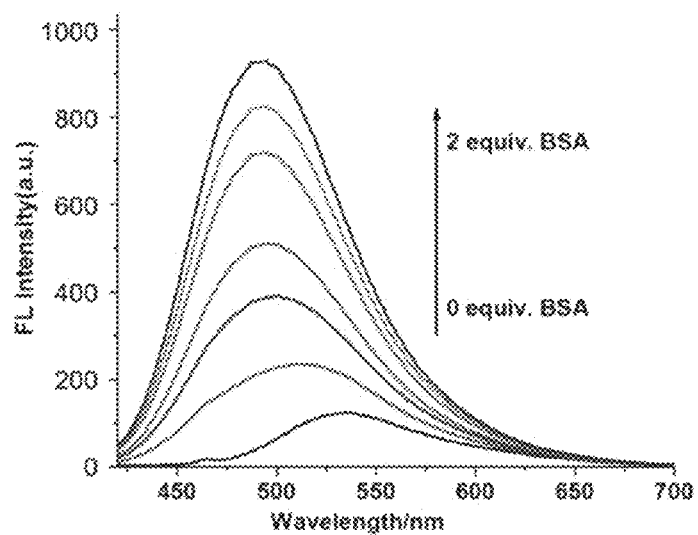
FIG. 4A provides a graph showing the fluorescence response of probe MC-Mito1 upon addition of different concentration of BSA in 1 mM HEPES buffer (1% DMSO).
Figure 4B:
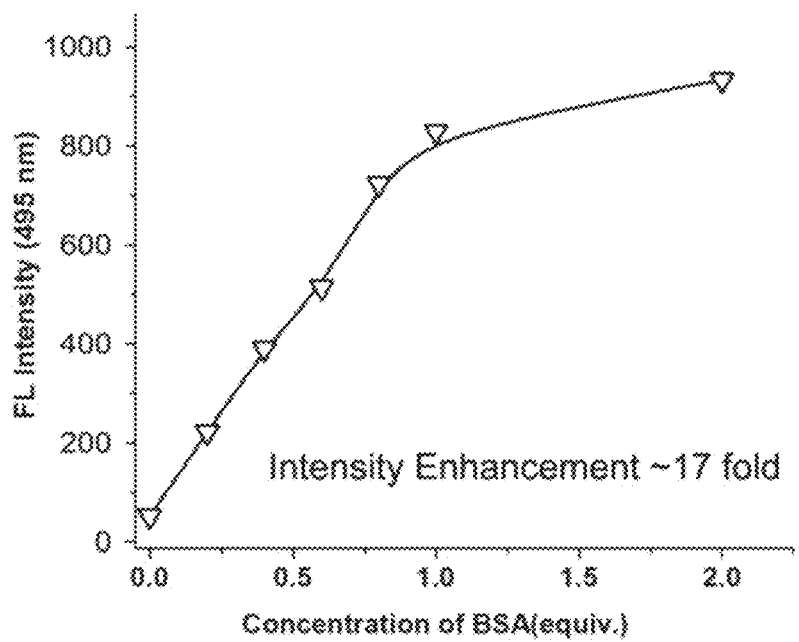
FIG. 4B provides a graph showing the fluorescence intensity changes of MC-Mito1 in the presence of increasing concentrations of BSA in 1 mM HEPES buffer (1% DMSO). [MC-Mito1]=[MC-Mito2]=2 µM, [BSA]=0~4 µM. $\lambda_{ex}$=400 nm.
Figure 4C:
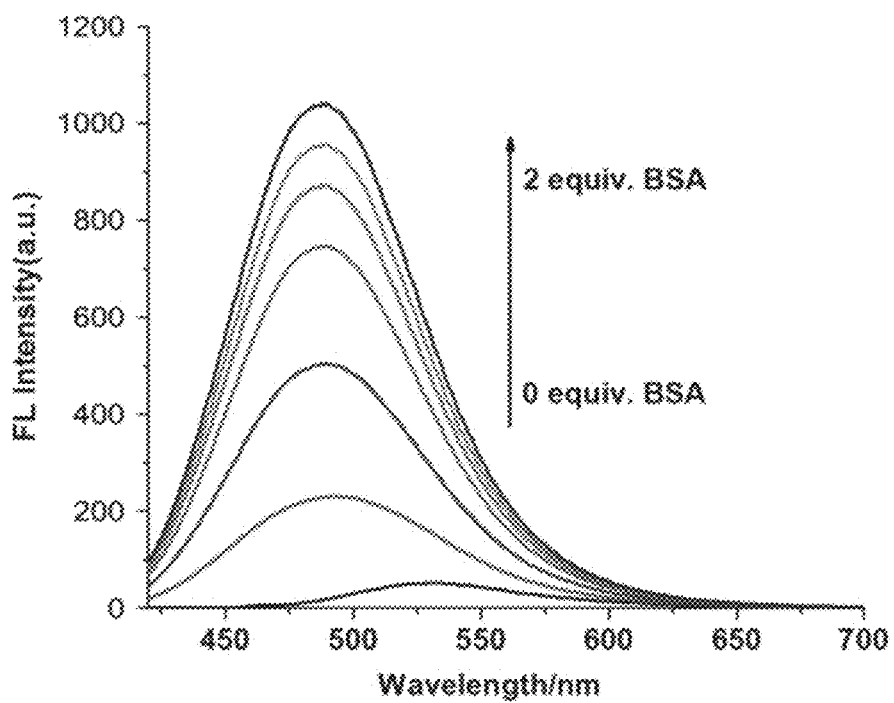
FIG. 4C provides a graph showing the fluorescence response of probe MC-Mito2 upon addition of different concentration of BSA in 1 mM HEPES buffer (1% DMSO).
Figure 4D:
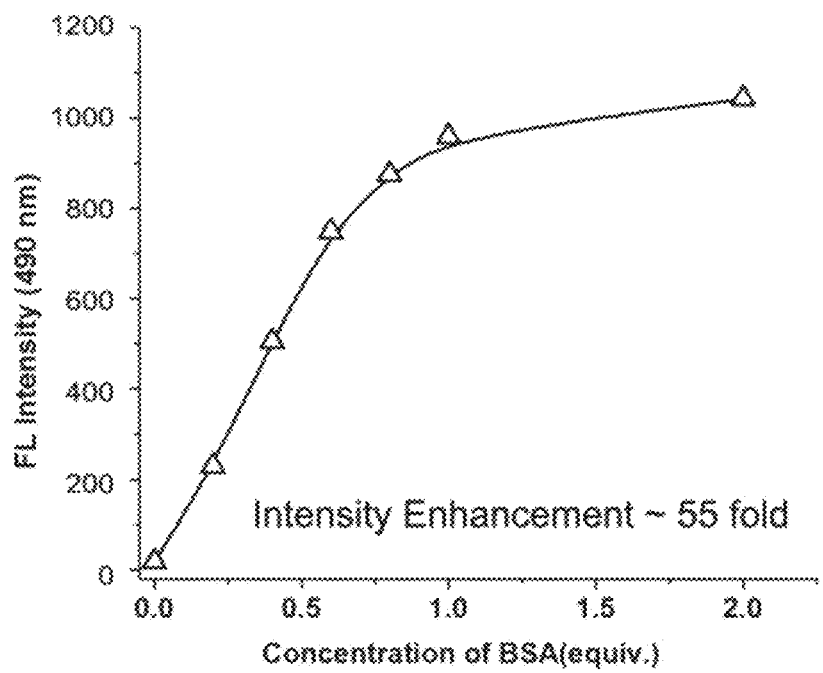
FIG. 4D provides a graph showing the fluorescence intensity changes of MC-Mito2 in the presence of increasing concentrations of BSA in 1 mM HEPES buffer (1% DMSO). [MC-Mito1]=[MC-Mito2]=2 µM, [BSA]=0~4 µM. $\lambda_{ex}$=400 nm.

In DMSO solution, MC-Mito1 and MC-Mito2 revealed the similar photophysical properties (FIG. 3), showing the absorption maxima at 373 nm and the emission maxima at 500 nm. The emission spectra of dyes were well separated from the absorption, revealing a large Stokes shifts (~127 nm) which is highly desirable for fluorescence imaging. The environment-sensitive properties of MC-Mito1 and MC-Mito2 were examined in different solvents. The results indicated that MC-Mito1 and MC-Mito2 showed classical positive solvatochromism features of flavone with a correlation between the emission maximum and relatively solvent polarity. The emission spectra shifted dramatically to longer wavelengths (from 450 nm to 540 nm) as the solvent polarity was increased. The probe's ability to shift the fluorescence from polar to non-polar environment could also facilitate the wash-free application, as the cell-bound dye gave emission at distinct wavelength from the free dye in aqueous.

MC-Mito1 and MC-Mito2 were nearly non-fluorescent in water (QYs <1%), due to specific H-bonding interaction of water solvents with H-bond acceptor carbonyl groups in flavone skeleton. However, upon addition of bovine serum albumin (BSA) into probe water solution, the fluorescence intensity increased sharply (FIG. 4A-D). After addition of 2 equivalent of BSA, the fluorescence intensity of MC-Mito1 at 495 nm was enhanced by about 17-fold, which was accompanied with a large blue-shift (from 540 nm to 495 nm, FIGS. 4A and 4B). The fluorescence intensity of MC-Mito2 at 490 nm was dramatically enhanced by about 55-fold upon addition of 2 equivalents of BSA, accompanied with 50 nm blue-shift as well. By using rhodamine 6G in ethanol (QY=95%) as a reference, the fluorescence quantum yield (QY) of MC-Mito1 and MC-Mito2 were determined to be 28% and 33%, respectively. The photophysical properties of MC-Mito1 and MC-Mito2 thus point to the potential of achieving the wash-free imaging methods, which normally require the probe to possess the following properties: (1) the fluorophore should be non-fluorescent (or weakly fluorescent) in water medium; (2) the fluorescence can be turned on when the fluorophore crosses the cell membrane into low-polar intracellular environment, which is essential for a high signal-to-noise ratio. To simply verify the imaging properties of these two dyes, zebrafish embryos at 4 hours post fertilization were stained with 5 μM of MC-Mito1 and MC-Mito2 for 15 min, and then directly used for imaging without washing process. The images clearly showed the fluorescence outline around the embryos, and very weak background signal. The high signal-to-noise ratio (>10) enables the simple wash-free in vivo fluorescence imaging.

Figure 5:
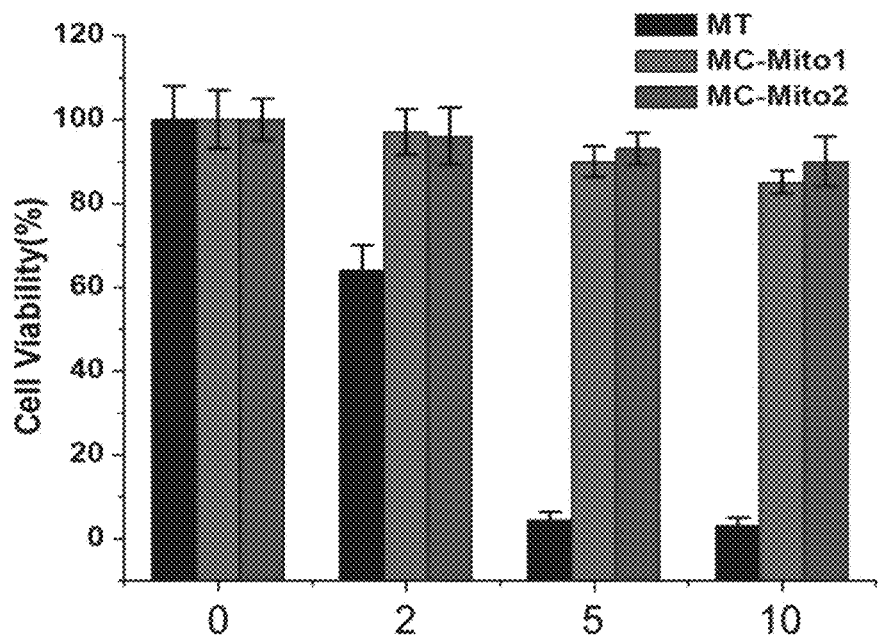
FIG. 5 provides a chart providing the results of cytotoxicity experiments of MC-Mito1, MC-Mito2 and MT at various concentrations in hMSCs (0, 2, 5, 10 µM) for 24 h.

Before the application for cell imaging, the cytotoxicity of MC-Mito1 and MC-Mito2 were evaluated by the widely used MTT assay to evaluate the tolerance of sensors to their working concentrations. The samples were incubated with 0, 2, 5, 10 μM MC-Mito1, MC-Mito2 and Mitotracker® red CMXRos (MT) for 24 h, respectively (FIG. 5). The results showed that the cell viabilities of MC-Mito1 and MC-Mito2 were close to 100%. In contrast, only less than 10% of the cells were viable after incubation with 5 μM of commercial mitochondrial dye MT for 24 hours. These results indicated that the wider working concentrations of MC-Mito1 and MC-Mito2 were much easier to manipulate in bioimaging than commercial MT, which tends to lose the specificity even cause cell apoptosis at higher concentration.

To assess their cell staining efficiencies, the hMSCs cells were incubated with MT, MC-Mito1 and MC-Mito2, respectively. Cell staining was continuously recorded in 3 min, 10 min and 25 min without washing process. It was found MC-Mito1 and MC-Mito2 quickly stained the living cells in 10 mins. In contrast, the MT acquired longer time to efficiently stain cells. The fluorescence signal of MC-Mito1 and MC-Mito2 from the 'blue channel' on fluorescence microscope (420-470 nm) were confined in cells with a negligible background signal from the culture medium, supporting the hypothesis that the flavone dyes gave higher emission in low-polar environment. Generally, the S/N ratios in fluorescent images were above 3, which could be considered acceptable for the discrimination of mitochondria. Therefore, this wash-free method could be a useful probe for real-time monitor of mitochondrial changes.

Figure 6A:
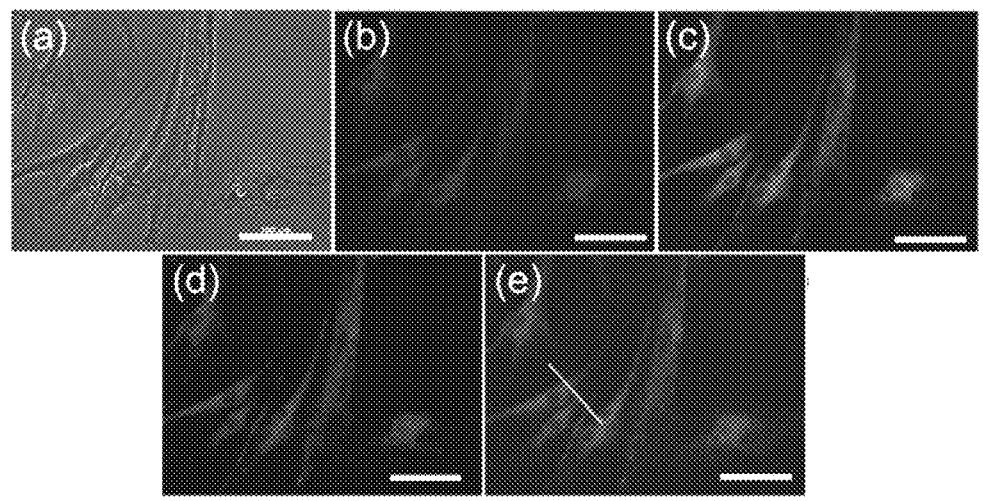
FIG. 6A provides fluorescence images of hMSCs co-stained with 25 nM of MT and 5 µM of MC-Mito1 for 25 min (a-k) Bright field (a), blue channel (b), green channel (c), red channel (d), and overlay images of blue channel and red channel (e). Scale bar: 100 µm.
Figure 6B:
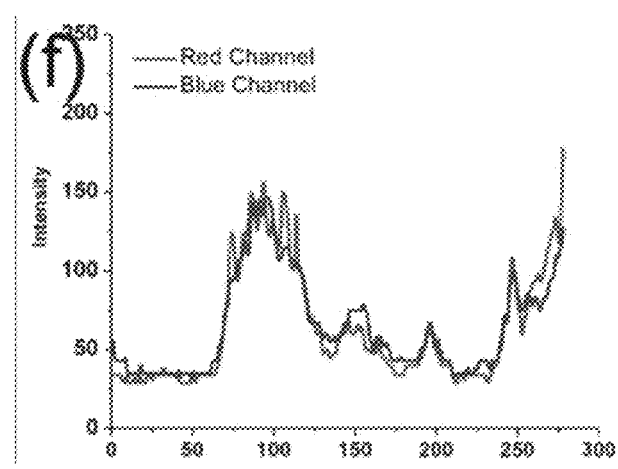
FIG. 6B provides a chart showing the profile of locations in the overlay images.
Figure 6C:
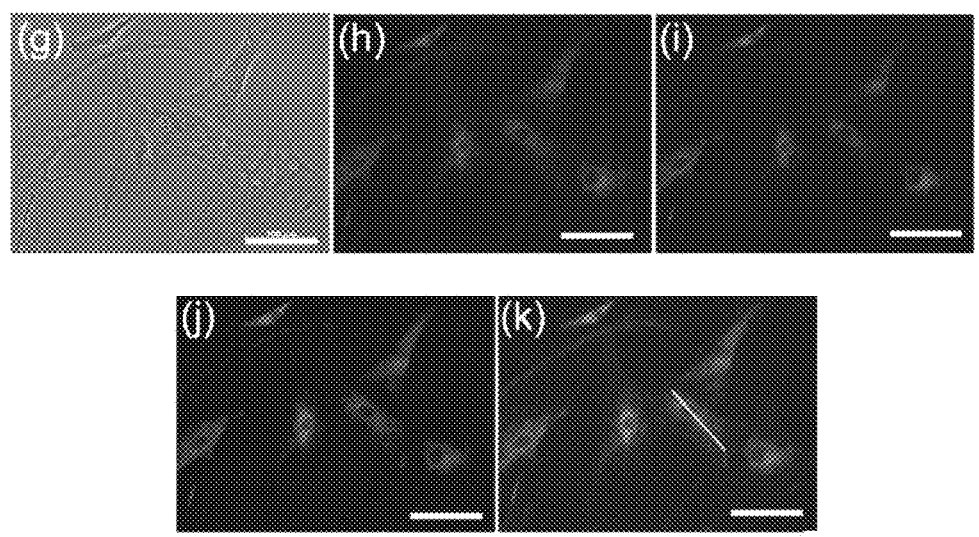
FIG. 6C provides fluorescence images of hMSCs co-stained with 25 nM of MT and 5 µM of MC-Mito2 for 25 min (g-l). Bright field (g), blue channel (h), green channel (i), red channel (j), and overlay images of blue channel and red channel (k). Scale bar: 100 µm.
Figure 6D:
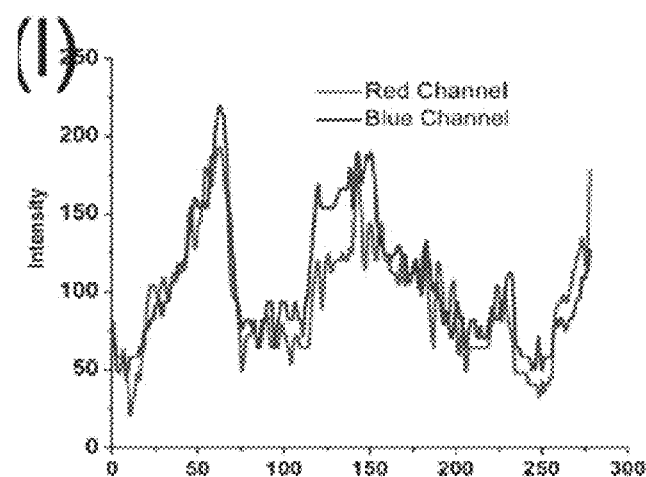
FIG. 6D provides a chart showing the profile of locations in the overlay images.

To determine the subcellular distribution of the probes in living cells, the MT were co-incubated with MC-Mito1 and MC-Mito2, respectively. FIG. 6A-D shows that the reticulum-like mitochondria were widespread across the entire cytoplasm. The subcellular regions stained with MC-Mito1 (blue and green channel) matched those stained with MT (red channel) very well. Similarly, MC-Mito2 staining pattern also matched well with MT as well (FIG. 6A-B). Without the targeting group, MC and MC-Br showed almost no co-localization with MT, confirming that the mitochondrial targetibility of these two probes highly depends on a targeting group that bears a positive charge as seen in the alkyltriphenylphosphonium bromide. Despite that the decrease of membranes potential will severely affect the direction and accumulation of cationic mitochondrial probes.

Figure 7:
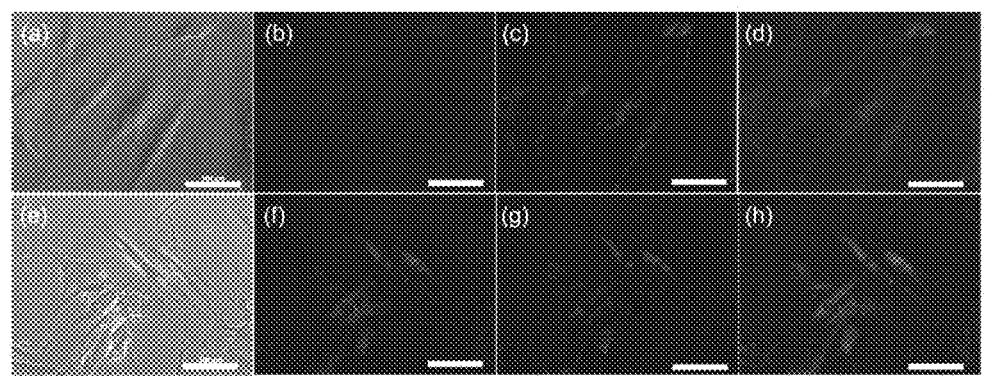
FIG. 7 provides fluorescence images of hMSCs that were pre-treated with 10 µM of CCCP for 30 min and then were co-stained with 25 nM of MT and 5 µM of MC-Mito1 for 25 min (a-d), 25 nM of MT and 5 µM of MC-Mito2 for 25 min (f-h). Bright field (a, e), blue channel (b, f), red channel (c, g), and overlay images of blue channel and red channel (d, h). Scale bar: 100 µm.
Figure 8:
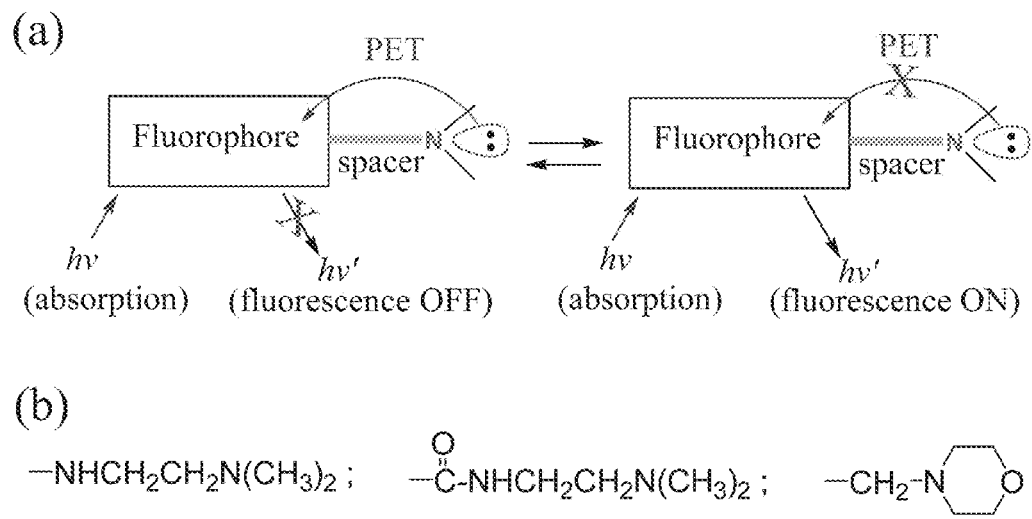
FIG. 8 (a) provides a scheme of the PET mechanism of amine-based fluorescence probes, and (b) describes common amine groups attached to fluorophores.

Mitochondria can continuously oxidize substrates and maintain a proton gradient across the lipid bilayer with very large membrane potential (−180 mV). The membrane potential as the major driving force enables the entrance and accumulation of the cationic species into mitochondria rather than cell plasma. CCCP is an uncoupler that causes rapid acidification of mitochondria and dysfunction of ATP synthase resulting in the decrease of mitochondrial membranes potential. To confirm the tolerances of MC-Mito1 and MC-Mito2, carbonyl cyanide m-chlorophenylhydrazone (CCCP) was used to treat the cells prior to the staining procedure. FIG. 7 showed that the fluorescent images of hMSCs with pre-treatment of 10 μM of CCCP for 30 min then stained with probes. It was found that the reticulum-like mitochondria are mostly transformed to small and dispersed fragments, due to that CCCP-induced collapse of mitochondrial membrane potential associated with the remodeling of mitochondrial cristae and the consequent occurrence of morphological change of mitochondriais.

After the treatment of CCCP, the uptake of MT was decreased by more than half and the specificity became worse (FIG. 7 images c and g). The MC-Mito1 showed extremely weaker imaging signal than that in normal cells and almost no more specificity to mitochondria (FIG. 7 image b). It was expected because CCCP-induced decrease of membranes potential will severely affect the direction and accumulation of cationic mitochondrial probes. The most of commercial mitochondrial probes are suffered by the similar limitation. However, under the same condition, the specificity and the sensitivity of MC-Mito2 to mitochondria are perfectly retained in CCCP-treated cells (FIG. 7 image f). Compared with MC-Mito1, MC-Mito2 has longer hydrophobic linker between the flavone dye and the cation. Since mitochondrial membrane is composed of phospholipid bilayers and proteins, the stronger lipophilicity has been supposed to play an important role in retaining the specificity of MC-Mito2 in CCCP-treated cells.

Synthesis 3-hydroxy-2-(4-morpholinophenyl)-4H-chromen-4-one (MC)

2-Hydroxyacetophenone (2.72 g, 20 mmol) was added to a solution of the 4-morpholinobenzaldehyde (3.82 g, 20 mmol) in ethanol (40 mL), then 20 ml of aqueous NaOH (8 g) solution was added slowly. The mixture was stirred at room temperature for 24 hours. $H_2O_2$ solution (8 ml of 30%) was slowly added into the reaction solution which was placed in an ice-water bath. After stirring at room temperature for 10 hours, the mixture was poured into ice-water and precipitate was collected via filtration, and washed with ethanol. The product was purified by recrystallization from ethanol. Yield=41%. $^1$H NMR (DMSO-d6, 300 MHz): 8.176 (d, J=9.0 Hz, 2H), 8.087 (d, J=7.5 Hz, 1H), 7.775 (m, 2H), 7.447 (m, 1H), 7.091 (d, J=9.3 Hz, 2H), 3.763 (t, 4H), 3.265 (t, 4H). $^{13}$C NMR (DMSO-d6, 75 MHz): 173.063, 154.741, 151.999, 146.507, 138.894, 133.555, 129.264, 125.183, 124.773, 121.855, 121.617, 118.636, 114.369, 66.370, 47.707.

(3-(2-(4-morpholinophenyl)-4-oxo-4H-chromen-3-yloxy)propyl)triphenylphosphonium bromide (MC-Mito1)

3-Hydroxy-2-(4-morpholinophenyl)-4H-chromen-4-one (MC) (0.646 g, 2 mmol), $CsCO_3$ (1.63 g, 5 mmol), (3-bromopropyl)triphenylphosphonium bromide (4.61 g, 10 mmol), and tetrabutylammonium bromide (1.61 g, 5 mmol) were dissolved in 10 ml DMF. The mixture was stirred at room temperature for 72 hours, and the resulting product was poured into water. The product mixture was extracted with 20 ml of DCM and dried with $Na_2SO_4$. After concentration under reduced pressure, the residue was purified by column chromatography (10:1 $CH_2Cl_2$/MeOH) to afford white solid. Yield=55%. $^1$H NMR (CDCl$_3$, 300 MHz) 8.150 (d, J=8.1 Hz, 1H), 8.000 (d, J=9.0 Hz, 2H), 7.851-7.673 (m, 16H), 7.515 (d, J=8.1 Hz, 1H), 7.369 (t, 1H), 6.999 (d, J=9.0 Hz, 2H), 4.236 (t, 2H), 4.110 (t, 2H), 3.871 (t, 4H), 3.271 (t, 4H), 2.214 (m, 2H). $^{13}$C NMR (CDCl$_3$, 75 MHz): 174.788, 156.724, 155.107, 152.626, 139.189, 135.055, 135.015, 134.950, 134.911, 133.881, 133.748, 133.248, 130.499, 130.398, 130.332, 129.951, 125.449, 124.524, 124.007, 120.410, 118.887, 117.954, 117.745, 114.219, 71.459, 66.624, 47.687, 24.263, 19.911. ESI-MS for $C_{40}H_{37}NO_4P^+$ [M+] calcd: 626.2455; found 626.2457

3-(6-bromohexyloxy)-2-(4-morpholinophenyl)-4H-chromen-4-one (MC-Br)

3-hydroxy-2-(4-morpholinophenyl)-4H-chromen-4-one (MC) (1.615 g, 5 mmol), $CsCO_3$ (3.26 g, 10 mmol), tetrabutylammonium bromide (3.22 g, 10 mmol) and 1,6-dibromohexane (6 g, 25 mmol) were added into 40 ml of DMF. The mixture was stirred at room temperature for 72 hours, and then was poured into 200 ml of water. The mixture was extracted with 50 ml of DCM and then washed with brine and water. After concentration under reduced pressure, the residue was purified by column chromatography (1:1 $CH_2Cl_2$/EtOAc). Yield=69%. $^1$H NMR (CDCl$_3$, 300 MHz) 8.262 (dd, J=8.1 Hz, J=1.5 Hz, 1H), 8.111 (d, J=9.3 Hz, 2H), 7.675 (m, 1H), 7.522 (d, J=8.1 Hz, 1H), 7.401 (m, 1H), 6.997 (d, J=9.3 Hz, 2H), 4.078 (t, 2H), 3.908 (t, 4H), 3.394 (t, 2H), 3.339 (t, 4H), 1.860-1.725 (m, 4H), 1.475-1.410 (m, 4H). $^{13}$C NMR (CDCl$_3$, 75 MHz) 174.871, 156.053, 155.118, 152.411, 139.731, 133.006, 130.008, 125.712, 124.400, 123.005, 121.368, 117.774, 113.892, 72.190, 66.643, 47.863, 33.764, 32.787, 29.906, 27.923, 25.176

(6-(2-(4-morpholinophenyl)-4-oxo-4H-chromen-3-yloxy)hexyl)triphenylphosphonium bromide (MC-Mito2)

3-(6-bromohexyloxy)-2-(4-morpholinophenyl)-4H-chromen-4-one (MC-Br) (0.97 g, 2 mmol), KI (0.33 g, 2 mmol), and triphenylphosphine (2.62 g, 10 mmol) was dissolved in 15 ml of toluene. The mixture was heated to reflux for 4 h, and then cooled to room temperature. The mixture was poured into 100 ml of ether to precipitate. The crude product was dissolved in a mixture solution of 15 ml DMF and 5 ml of aqueous NaBr (3 g). The mixture was stirred for 3 hours at 50° C., and then was extracted with 50 ml DCM and washed with 100 ml water. The solution was concentrated to 5 ml and poured into 50 ml ether. The precipitate could be used directly without further purification. Yield=63%. $^1$H NMR (CDCl$_3$, 300 MHz): 8.167 (dd, J=8.1 Hz, J=1.5 Hz, 1H), 8.087 (d, J=9.0 Hz, 2H), 7.87-7.609 (m, 16H), 7.519 (d, J=8.4 Hz, 1H), 7.370 (t, 1H), 7.011 (d, J=9.3 Hz, 2H), 3.943 (t, 2H), 3.884 (t, 4H), 3.761 (m, 2H), 3.341 (t, 4H), 1.735-1.526 (m, 4H). $^{13}$C NMR (CDCl$_3$, 75 MHz): 174.844, 156.289, 155.091, 152.516, 139.571, 135.050, 135.012, 133.765, 133.633, 133.046, 130.585, 130.503, 130.419, 129.831, 125.453, 124.375, 124.169, 120.851, 118.810, 117.883, 117.672, 114.027, 71.963, 66.651, 47.773, 30.104, 29.896, 29.579, 25.364, 23.332, 22.471. ESI-MS for $C_{43}H_{43}NO_4P^+$[M+] calcd: 668.2924; found 668.2913.

Fluorescence Quantum Yield

The fluorescence quantum yields were obtained using rhodamine 6G (sigma) as the standard ($\Phi_{fl}$=0.95, ethanol). The fluorescence quantum yields can be calculated by using the following Eq:

$$\Phi_s = \Phi_r \times (A_r \times n_s^2 \times F_s)/(A_s \times n_r^2 \times F_r)$$

where the subscripts s and r refer to the sample and the standard, respectively. $\Phi$ is the quantum yield, F is the integrated emission intensity, A is the absorbance, and n is the refractive index.

Zebrafish Breeding and Imaging

All animal related procedures were approved by the Care and Use of Animals in Research Committee at the University of Akron. Zebrafish (*Danio rerio*) were maintained as described in the Zebrafish Book by the University of Oregon. Zebrafish were kept at 28.5° C. and maintained at optimal breeding conditions. For mating, male and female zebrafish were maintained in one tank at 28.5° C. on a 12 h light/12 h dark cycle and then the spawning of eggs were triggered by giving light stimulation in the morning. Almost all the eggs were fertilized immediately. The zebrafishs were maintained in E3 embryo medium (15 mM NaCl, 0.5 mM KCl, 1 mM $MgSO_4$, 1 mM $CaCl_2$, 0.15 mM $KH_2PO_4$, 0.05 mM $Na_2HPO_4$, 0.7 mM $NaHCO_3$, $10^{-5}$% methylene blue; pH 7.5). The 4 hpf zebrafish embryos were incubated with E3 medium containing 5 μmol/L of MC-Mito1 and MC-Mito2 for 15 min, respectively. The fluorescence images of embryos were directly taken without wash process.

Cell Culture and Imaging

Human mesenchymal stem cells (hMSCs) (Lonza, Walkersville, Md.) were cultured in serum-containing MSCBM medium (Lonza) supplemented with MSCGM SingleQuots (Lonza) according to manufacturer's specifications. hMSCs (Passage 5) were seeded at a density of $5.0 \times 10^4$ cell/$cm^2$. For co-staining experiments, the hMSCs were seeded on 12-well plate, cultured in MSCBM medium (Lonza) supplemented with MSCGM SingleQuots (Lonza), and incubated with 5 μM MC and 25 nM Mitotracker® red CMXRos (MT), 5 μM MC-Br and 25 nM MT, 5 μM MC-Mito1 and 25 nM MT, 5 μM MC-Mito2 and 25 nM MT for 25 min at 37° C., respectively. Each well contains 1 ml of medium and 0.05 ml DMSO (dissolving probe). The cell imaging was obtained on a Zeiss inverted fluorescence microscopy with X-Cite Series 120Q. The blue channel filter: excitation 365 nm, beam splitter FT 395 nm, emission 445/50 nm. The green channel filter: excitation 450-490 nm, beam splitter FT 510 nm, emission 515-565 nm. The red channel filter: excitation 587/25 nm, beam splitter FT 605 nm, emission 647/70 nm.

Cytotoxicity Determined by MTT Method.

The hMSCs were seeded in 12-well plates at a density of $5.0 \times 10^4$ cell/$cm^2$. After 24 h incubation, the cells were exposed to a series of doses of probe MC-Mito1 or MC-Mito2, and MT at 37° C. The concentration of MT (0, 2, 5, 10 μM) was similar as reported in literature.[28] After 24 hours, MTT solution (sigma) was added and kept 3 h in the incubator. MTT solubilization solution was then added into each well and the plate was gently shaken for 10 min at room temperature. The absorbance of MTT in the sample well was determined by subtracting the absorbance of the sample well from corresponding control well. Cell viability was expressed by the ratio of the absorbance of MTT in the sample wells to that of the cells incubated with culture medium only.

Effects of CCCP on Uptake of Dyes

The hMSCs were treated with 10 μM carbonyl cyanide m-chlorophenylhydrazone (CCCP) for 30 min. and then were washed with fresh medium. After that, the cells were incubated with 5 μM MC-Mito1 and 25 nM MT, 5 μM MC-Mito2 and 25 nM MT for 25 min at 37° C., respectively. After staining, the cells were imaged by microscope without PBS solution washing procedure.

Lysosome Imaging

Figure 9:
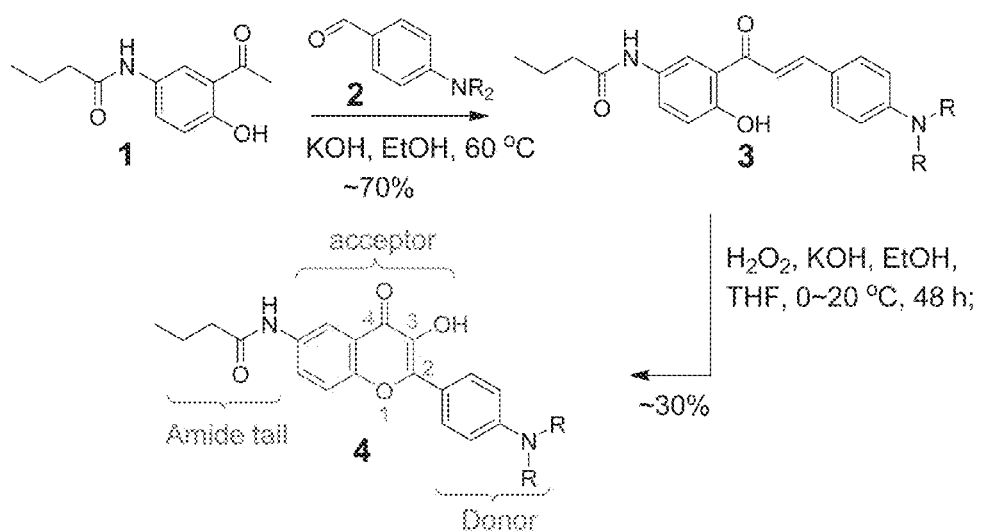
FIG. 9 provides a scheme for the synthesis of flavonoid compound 4.

With reference to FIG. 9, a series of new flavonoid compounds 4 were synthesized from 3 by using base catalyzed epoxidation of the conjugated double bond (Algar-Flynn-Oyamada reaction) (FIG. 9). The conjugated ketone 3 was obtained by Claisen-Schmidt condensation between aldehyde 2 and ketone 1. The developed fluorescent probes DMAF, DEAF and DPAF includes electron donor-acceptor groups, which influence the optical properties. The probe also include an amide, which could tune the probe's interaction with proteins.

Figure 10:
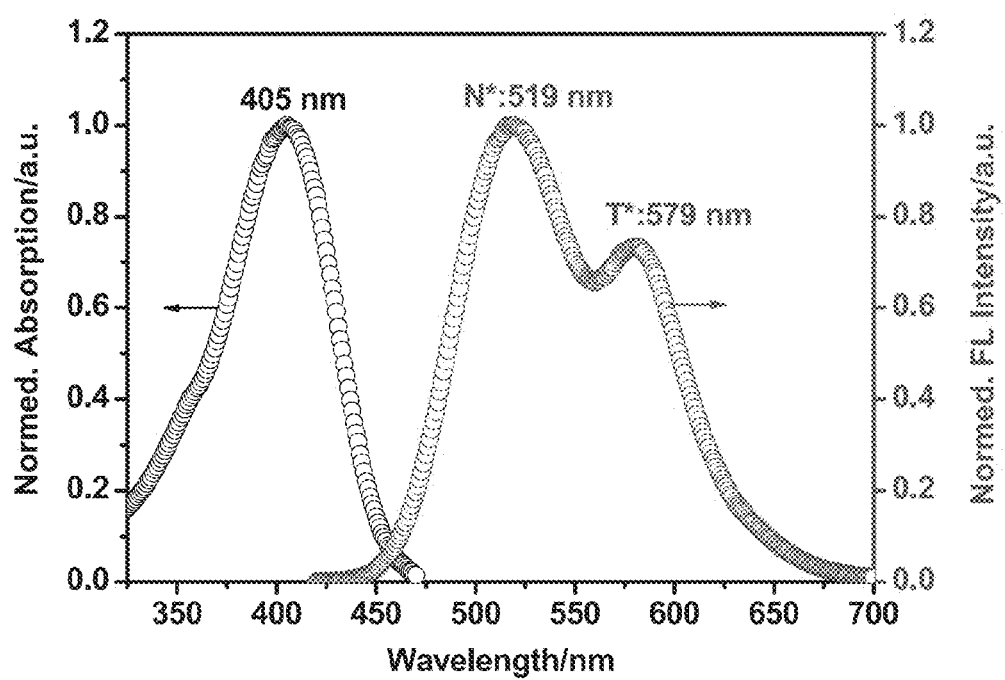
FIG. 10 is a chart showing the normalized UV and FL spectra of DMAF (=12a) in DMSO solution ([DMAF]=10 µM). N*: Normal type emission, T*: Tautomer type emission. Exicitation wavelength: 400 nm.

The absorbance and fluorescence spectra of DMAF (4a) and DEAF (4b) were investigated in DMSO. As shown in FIG. 10, DMAF showed the absorption maxima at 405 nm and the emission maxima at 519 nm, while DEAF showed the similar optical properties, with the absorption maxima at 412 nm and the emission maxima at 510 nm. Both DMAF and DEAF gave two fluorescence bands corresponding to the excited normal form (N*) and the tautomeric form (T*) associated with excited state intramolecular proton transfer (ESIPT).[8] By using rhodamine 6G in ethanol (QY=95%) as a reference, the fluorescence quantum yield (QY) of DMAF and DEAF were determined to be 26% and 18%, respectively. Upon excitation via photon irradiation, the dipole moment increased dramatically because of the charge transfer from the Donor-Acceptor structure of the flavonoids. The ESIPT process of DMAF and DEAF combining with the charge transfer process, contributed significantly to Stokes shift (~170 nm) increase. The large Stokes shifts of these flavonoids could efficiently reduce the spectra over lapping, thus be highly desirable for fluorescence imaging.

Figure 11:
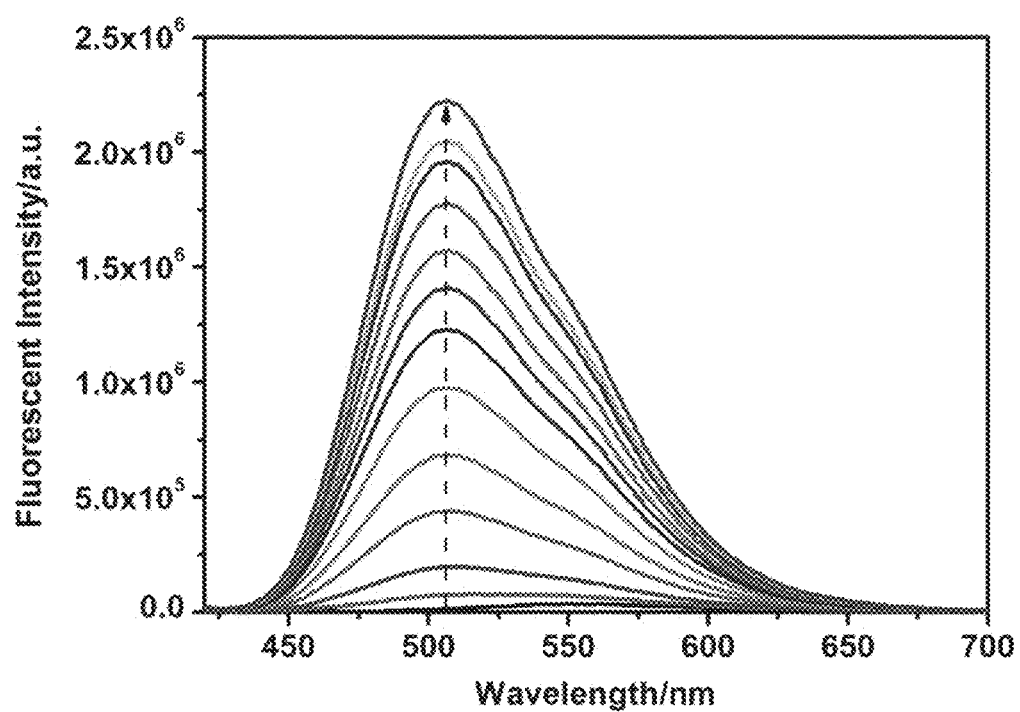
FIG. 11 is a chart showing fluorescence spectra of DMAF ([DMAF]=10 µM, 1 mM HEPES buffer containing 1% DMSO, pH=7.4) upon addition of different concentration of BSA ([BSA]=0-10 µM, 1 mM HEPES).
Figure 12:
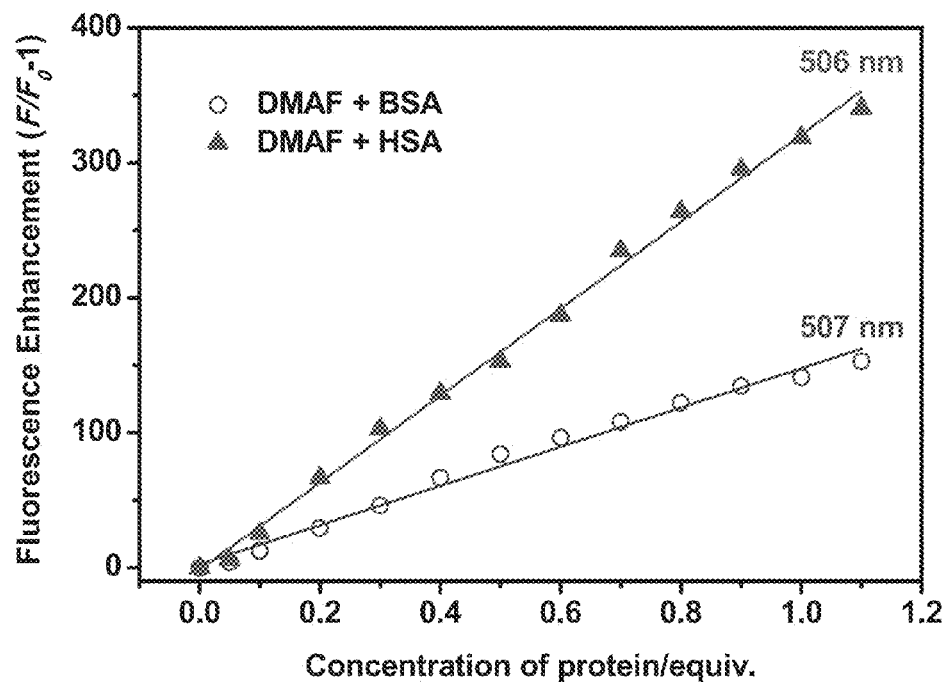
FIG. 12 is a chart showing fluorescence enhancement of DMAF in the presence of increasing concentrations of serum albumin FIG. 13A provides images showing co-localization of hMSCs and SH-SY5Y cells stained with DMAF and Lyso-Tracker® red DND-99. (a) From left column to right column; bright-field, FL imaging of DMAF ($\lambda_{em}$=515-565 nm, green emission), FL imaging of Lyso-Tracker ($\lambda_{em}$=610-680 nm, red emission) and overlay fluorescence images of green and red emission. Scale Bar: 100 µm.

Strong binding with serum albumin was considered as a significant feature for flavonoids. Due to hydrogen-bonding interaction of water solvents with hydrogen-bond acceptor carbonyl groups in flavonoid skeleton, the fluorescence of DMAF was nearly completely quenched by water (FIGS. 11 and 12). Upon addition of serum albumin, the fluorescence of the flavonoid dyes was found to be remarkably enhanced. The fluorescence enhancement of DMAF in the presence of 1.0 equiv of bovine serum albumin (BSA) and human serum albumin (HSA) was calculated as 141 and 319 fold, respectively. The fluorescence enhancement of DEAF towards 1.0 equiv of BSA and HSA were 150 and 80 fold, with the detection limits to be 0.20 and 0.38 μM, respectively. The detection limits of two flavonoids were much lower than serum albumin concentration in blood plasma, indicating strong interaction with bioprotein.

Figure 13A:
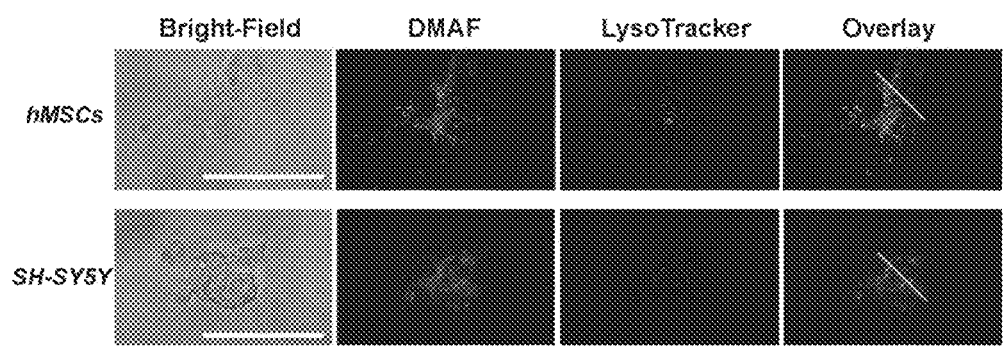
FIG. 13B provides a graph showing the fluorescent intensity profiles across co-stained hMSCs.
FIG. 13C provides a graph showing the intensity profiles across co-stained SH-SY5Y cells.
Figure 13B:
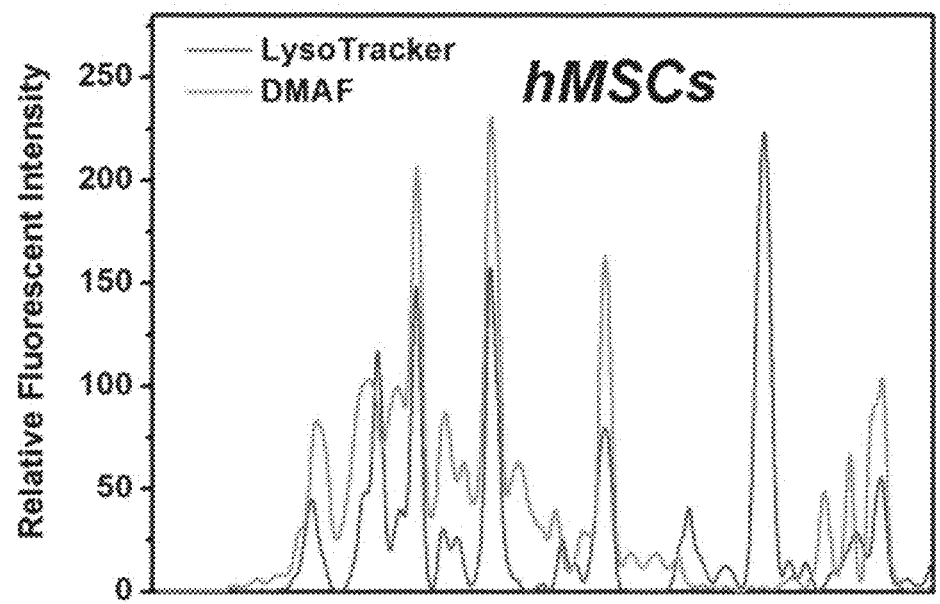
Figure 13C:
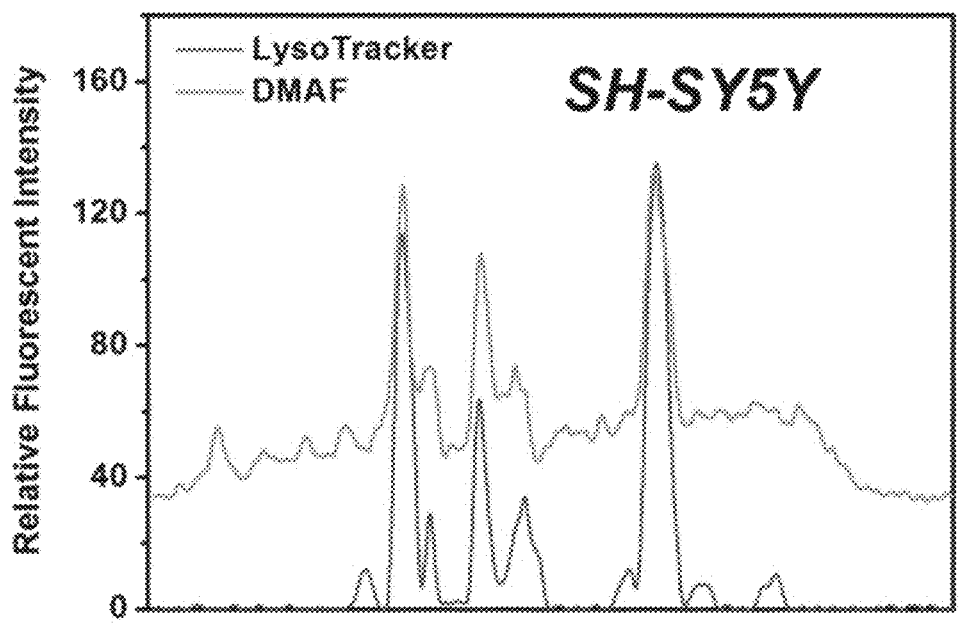

Good response of flavonoid dyes to proteins encouraged us to further examine their response to biological cells. To evaluate the subcellular distribution of the DMAF, the flavonoid dye was applied to human mesenchymal stem cells (hMSCs) and Human neuroblastoma cells (SH-SY5Y). The cells were first incubated with DMAF at 5 μM for 30 min, followed by incubation for 6 hours at 37° C. for intracellular relocation of probe molecule in cytoplasm. The lysosome-specific staining probe LysoTracker® red DND-99 (50 nM) was added and co-stained for 30 minutes. As shown in FIG. 13A, the stain with DMAF revealed some bright spots within the cells, indicating the potential for detection of subcellular regions. The subcellular regions stained with DMAF matched those stained with LysoTracker very well, showing that the bright spots by flavonoid stain are associated with lysosome organelles. The changes in the intensity profile of linear regions of co-stained cells (DMAF and LysoTracker) tended toward synchronization in both hMSCs and SH-SY5Y cells (FIGS. 13B and 13C). The results thus indicated that the DMAF was a reliable bioprobe for lysosomes imaging.

Cell Culture and Staining.

The hMSCs (Lonza, Walkersville, Md.) were cultured in serum-containing MSCBM medium (Lonza) supplemented with MSCGM SingleQuots (Lonza) according to manufacturer's specifications. The hMSCs were seeded in MSCBM medium on a 6-well plate, and then incubated with 5 μM DMAF (or DEAF) for 30 minutes, respectively. After staining process, the hMSCs were washed with MSCBM medium for 3 times, and then were continuously cultured in MSCBM medium at 37° C. The fluorescent images were captured at 0 hour, 6 hours, and 12 hours after dye staining, respectively. For the co-staining experiments, the cells were incubated with 5 μM DMAF for 30 min at 37° C., and then were washed 3 times with medium. After 6 hours, the cells were incubated with 50 nM LysoTracker® red DND-99 for 30 minutes. After washing with water, the cells were imaged.

Various modifications and alterations that do not depart from the scope and spirit of this invention will become apparent to those skilled in the art. This invention is not to be duly limited to the illustrative embodiments set forth herein.

What is claimed is:

1. A flavonoid compound defined by the formula

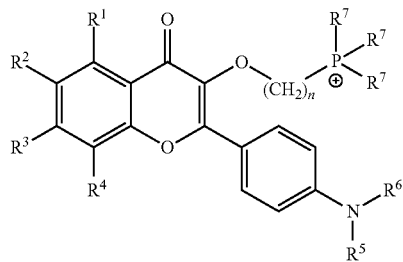

where each $R^1$-$R^4$ is individually an organic group or an hydrogen atom, $R^5$ and $R^6$ are each individually an organic group or an hydrogen atom or where $R^5$ and $R^6$ combine to form a single organic group, each $R^7$ is individually an organic group, and n is about 3 to 10 units.

2. The flavonoid of claim 1, where the flavonoid compound is defined by the formula

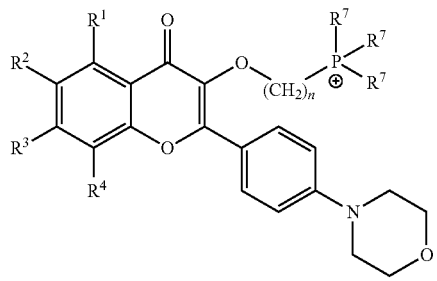

where each $R^{10}$-$R^4$ is individually an organic group or an hydrogen atom, each $R^7$ is individually an organic group, and n is about 3 to 10 units.

3. The flavonoid of claim 1, where the flavonoid compound is defined by the formula

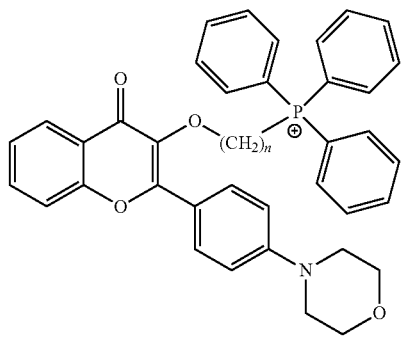

where n is about 3 to 10 units.

4. The flavonoid of claim 1, where the flavonoid compound is defined by the formula

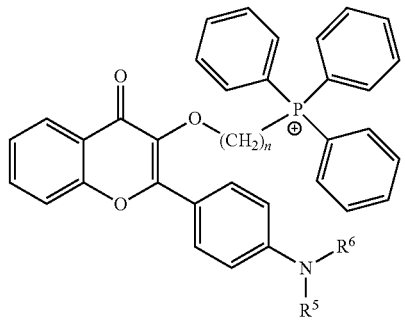

where $R^5$ and $R^6$ are each individually an organic group or an hydrogen atom or where $R^5$ and $R^6$ combine to form a single organic group and n is about 3 to 10 units.

5. A flavonoid compound defined by the formula

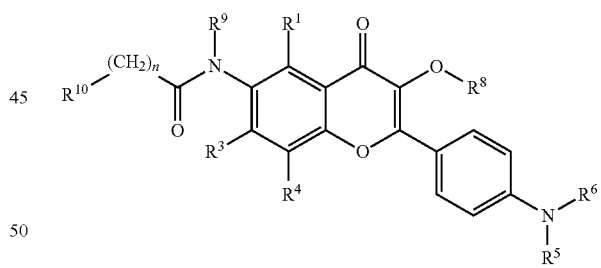

where each $R^1$, $R^3$, and $R^4$ is individually an organic group or an hydrogen atom, $R^5$ and $R^6$ are each individually an organic group or an hydrogen atom or where $R^5$ and $R^6$ combine to form a single organic group, $R^8$ is an organic group or a hydrogen atom, $R^9$ is an organic group or a hydrogen atom, $R^{11}$ and $R^{12}$ are each individually an organic group or an hydrogen atom or where $R^{11}$ and $R^{12}$ combine to form a single organic group, and n is about 1 to 6 units.

6. A method of imaging an organelle comprising
combining a mitochondrion and a flavonoid compound and allowing the flavonoid compound to stain the mitochondrion, where the flavonoid compound is defined by the formula

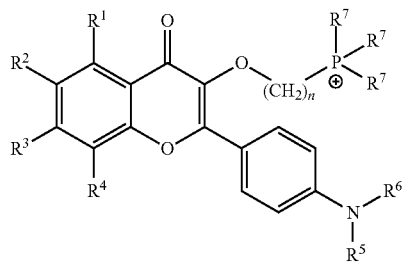
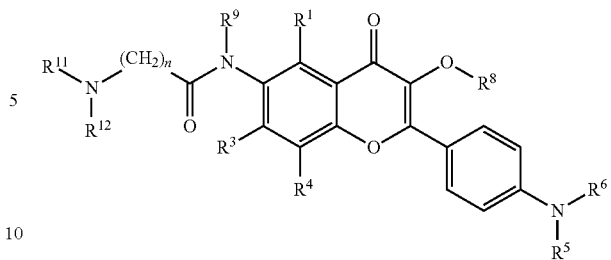

where each $R^1$-$R^4$ is individually an organic group or an hydrogen atom, $R^5$ and $R^6$ are each individually an organic group or an hydrogen atom or where $R^5$ and $R^6$ combine to form a single organic group, each $R^7$ is individually an organic group, and n is about 3 to 10 units;

irradiating the stained mitochondrion with an excitation wavelength that excites the flavonoid compound and induces a fluorescence response; and capturing an image of the fluorescence response.

7. The method of claim 6, where the mitochondrion is an isolated cell-free mitochondrion.

8. The method of claim 6, where the mitochondrion is present in a eukaryotic cell.

9. The method of claim 8, where the eukaryotic cell is a stem cell.

10. The method of claim 6, where the step of allowing the flavonoid compound to stain the mitochondrion is performed by incubating a mitochondrion with about 0.02 μM to about 10 μM of the flavonoid compound at about 37° C. for about 25 min in a growth medium.

11. A method of imaging an organelle comprising
combining a lysosome of a eukaryotic cell and a flavonoid compound and allowing the flavonoid compound to stain the lysosome, where the flavonoid compound is defined by the formula where each $R^1$, $R^3$, and $R^4$ is individually an organic group or a hydrogen atom, $R^5$ and $R^6$ are each individually an organic group or a hydrogen atom or where $R^5$ and $R^6$ combine to form a single organic group, $R^8$ is an organic group or a hydrogen atom, $R^9$ is an organic group or a hydrogen atom, $R^{11}$ and $R^{12}$ are each individually an organic group or a hydrogen atom or where $R^{11}$ and $R^{12}$ combine to form a single organic group, and n is about 1 to 6 units;

irradiating the stained lysosome with an excitation wavelength that excites the flavonoid compound and induces a fluorescence response; and capturing an image of the fluorescence response.

12. The method of claim 11, where the lysosome is an isolated cell-free lysosome.

13. The method of claim 11, where the lysosome is in a eukaryotic cell.

14. The method of claim 13, where the eukaryotic cell is a stem cell.

15. The method of claim 11, where the step of allowing the flavonoid compound to stain the lysosome is performed by incubating a lysosome with about 0.02 μM to about 10 μM of the flavonoid compound at about 37° C. for about 25 min in a growth medium.

* * * * *